United States Patent [19]
Caldwell et al.

[11] Patent Number: 5,861,423
[45] Date of Patent: Jan. 19, 1999

[54] PHARMACEUTICAL COMPOSITIONS INCORPORATING ARYL SUBSTITUTED OLEFINIC AMINE COMPOUNDS

[76] Inventors: William Scott Caldwell, 1270 Yorkshire Rd., Winston-Salem, N.C. 27106; Gary Maurice Dull, 6025 Shallowford Rd., Lewisville, N.C. 27023; Merouane Bencherif, 1140 Lazyboy La., Winston-Salem, N.C. 27103; Patrick Michael Lippiello, 1233 Arboretum, Lewsiville, N.C. 27023

[21] Appl. No.: 804,248

[22] Filed: Feb. 21, 1997

[51] Int. Cl.$^6$ .................................................. A61K 31/44
[52] U.S. Cl. ........................... 514/351; 514/345; 514/357
[58] Field of Search .................... 514/345, 351, 514/357

[56] References Cited

U.S. PATENT DOCUMENTS

| | | | |
|---|---|---|---|
| 5,212,188 | 5/1993 | Caldwell et al. | |
| 5,227,391 | 7/1993 | Caldwell et al. | 514/343 |
| 5,242,935 | 9/1993 | Lippiello et al. | 514/343 |
| 5,346,906 | 9/1994 | Baker et al. | 514/305 |
| 5,559,124 | 9/1996 | Bencherif et al. | 514/305 |
| 5,583,140 | 12/1996 | Bencherif et al. | 514/299 |
| 5,597,919 | 1/1997 | Dull et al. | 544/242 |
| 5,616,716 | 4/1997 | Dull et al. | |

FOREIGN PATENT DOCUMENTS

WO96/31475  10/1996  WIPO.

OTHER PUBLICATIONS

Henrich et al.; "Microcirculatory Effects of Nicotine and Related Alkaloids"; *Klin Wochenchr,* 62(II):92–100 (1984).

Gibson et al.; "Principal Components Describing Biological Activities and Molecular Diversity of Heterocyclic Aromatic Ring Fragments"; *J. Med. Chem.,* 39:4065–4072 (1996).

Wilson, Jr. et al.; "Nicotine–Like Actions of cis–Metanicotine and trans–Metanicotine"; *J. of Pharmacology and Exper. Therapeutics,* 196(3):685–696 (1976).

Baron; "Cigarette smoking and Parkinson's Disease"; *Neurology,* 36:1490–1496 (1986).

Decina et al.; "Cigarette Smoking and Neuroleptic–Induced Parkinsonism"; *Biol. Psychiatry,* 28(6):502–508 (1990).

Faraone et al.; "An Exploratory Study of ADHD among Second–Degree Relatives of ADHD Children"; *Biol. Psychiatry,* 35(6):398–402 (1994).

Giacobini; "Pharmacotherapy of Alzheimer's Disease: New Drugs and Novel Strategies"; *Therapeutics,* 61:529–538 (1993).

Hall et al.; "Effects of Nicotine on the Release of $^3$H–Noradrenaline from the Hypothalamus"; *Biochemical Pharmacology,* 21:1829–1838 (1972).

Hamon: "Neuropharmacology of anxiety: perspectives and prospects"; *TiPS,* 15:36–39 (1994).

Harsing, Jr. et al.; "Dopamine Efflux from Striatum After Chronic Nicotine: Evidence for Autoreceptor Desensitization"; *J. of Neurochemistry,* 59(1):48–54 (1992).

Newhouse et al.; "The role of nicotine and nicotinic mechanisms in neuropsychiatric disease"; *British J. of Addiction,* 86:521–526 (1991).

Onaivi et al.; "Chronic Nicotine Reverses Age–Associated Increases in Tail–Flick Latency and Anxiety in Rats"; *Life Sciences,* 54(3):193–202 (1994).

Pomerleau et al.; "The Effects of Cigarette Smoking on Pain and Anxiety"; *Addictive Behaviors,* 9:265–271 (1984).

Rapier et al.; "Stereoselective Nicotine–Induced Release of Dopamine from Striatal Synaptosomes: Concentration Dependence and Repetitive Stimulation"; *J. Neurochem.,* 50(4):1123–1130 (1988).

Rowell; "Current Concepts on the Effects of Nicotine on Neurotransmitter Release in the Central Nervous System"; *Adv. Behav. Biol.,* 31:191–208 (1987).

Rowell et al.; "Nicotinic Stimulation of [$^3$H]Acetylcholine Release from Mouse Cerebral Cortical Synaptosomes"; *J. Neurochem.,* 43(6):1593–1598 (1984).

Sandor et al.; "Effect of Nicotine on dopaminergic–cholinergic interaction in the striatum"; *Brain Res.,* 567:313–316 (1991).

Sherwood; "Effects of Nicotine on Human Psychomotor Performance"; *Human Psychopharmacology,* 8:155–184 (1993).

Sjak–Shie et al.; "Effects of chronic nicotine and pilocarpine administration on neocortocal neuronal density and [$^3$H] GABA uptake in nucleus basalis lesioned rats"; *Brain Res.,* 624:295–298 (1993).

Toth et al.; "Effect of Nicotine of Extracellular Levels of Neurotransmitters Assessed by Microdialysis in Various Brain Regions"; *Neurochem. Res.,* 17(3):265–271 (1992).

Vizi; "Acetylcholine release from guinea–pig ileum by parasymathetic ganglion stimulants and gastrin–like polypeptides"; *Br. J. Pharmac.,* 47:765–777 (1973).

Wagner et al.; "Does Smoking Reduce the Risk of Neuroleptic Parkinsonoids?"; *Pharmacopsychiat.,* 21:302–303 (1988).

Lippiello et al.; "RJR–2403: A Nicotinic Agonist with CNS Selectivity II. In Vivo Characterization"; *J. Pharmacol. Exper. Therapeutics,* 279(3):1422–1429 (1996).

Bencherif et al.; "RJR–2403: A Nicotinic Agonsist with CNS Selectivity I: In Vitro Characterization"; *J. Pharmacol. Exper. Therapeutics,* 279(3):1413–1421 (1996).

(List continued on next page.)

*Primary Examiner*—William R. A. Jarvis

[57] ABSTRACT

Patients susceptible to or suffering from central nervous system disorders (e.g., Alzheimer's disease, Parkinson's disease, Tourette's syndrome, attention deficit disorder or schizophrenia) are treated by administering an effective amount of an aryl substituted olefinic amine compound. Exemplary compounds include (E)-N-methyl-4-[3-(5-benzyloxypyridin)yl]-3-buten-1-amine, (E)-N-methyl-4-[3-(5-phenoxypyridin)yl]-3-buten-1-amine, and (E)-N-methyl-4-[3-(5-phenylpyridin)yl]-3-buten-1-amine.

12 Claims, No Drawings

OTHER PUBLICATIONS

Héry et al.; "Control of the Release of Newly Synthetized 3H–5–Hydroxytryptamine by Nicotinic and Muscarinic Receptors in Rat Hypothalamic Slices"; *Naunyn–Schmiedeberg's Arch. Pharmacol.*, 296:91–97 (1977).

Pullan et al.; "Transdermal Nicotine for Active Ulcerative Colitis"; *New England J. Med.*, 330(12):811–815 (1994).

Frank et al.; "Palladium–Catalyzed Vinylic Substitution Reactions with Heterocyclic Bromides"; *J. Org. Chem.*, 43(15):2947–2949 (1978).

Abstract S39: Sanberg et al.; "Beneficial Effects of Nicotine in Tourette's Syndrome"; *Int'l Symposium on Nicotine: The Effects of Nicotine on Biological Systems II, Montreal Canada, Jul. 21–24, 1994*.

PHARMACEUTICAL COMPOSITIONS INCORPORATING ARYL SUBSTITUTED OLEFINIC AMINE COMPOUNDS

BACKGROUND OF THE INVENTION

The present invention relates to pharmaceutical compositions, and particularly pharmaceutical compositions incorporating compounds which are capable of affecting nicotinic chlorinergic receptors. The present invention also relates to methods for treating a wide variety of conditions and disorders, and particularly conditions and disorders associated with dysfunction of the central and automatic nervous systems.

Nicotine has been proposed to have a number of pharmacological effects. See, for example, Pullan et al. *N. Engl. J. Med.* 330: 811–815 (1994). Certain of those effects may be related to effects upon neurotransmitter release. See for example, Sjak-shie et al., *Brain Res.* 624: 295 (1993), where neuroprotective effects of nicotine are proposed. Release of acetylcholine and dopamine by neurons upon administration of nicotine has been reported by Rowell et al., *J. Neurochem.* 43: 1593 (1984); Rapier et al., *J Neurochem.* 50: 1123 (1988); Sandor et al., *Brain Res.* 567: 313 (1991) and Vizi, *Br. J Pharmacol.* 47: 765 (1973). Release of norepinephrine by neurons upon administration of nicotine has been reported by Hall et al., *Biochem. Pharmacol.* 21: 1829 (1972). Release of serotonin by neurons upon administration of nicotine has been reported by Hery et al., *Arch. Int. Pharmacodyn. Ther.* 296: 91 (1977). Release of glutamate by neurons upon administration of nicotine has been reported by Toth et al., *Neurochem Res.* 17: 265 (1992). In addition, nicotine reportedly potentiates the pharmacological behavior of certain pharmaceutical compositions used for the treatment of certain CNS disorders. See, Sanberg et al., *Pharmacol. Biochem. & Behavior* 46: 303 (1993); Harsing et al., *J. Neurochem.* 59: 48 (1993) and Hughes, *Proceedings from Intl. Symp. Nic.* S40 (1994). Furthermore, various other beneficial pharmacological effects of nicotine have been proposed. See, Decina et al., *Biol. Psychiatry* 28: 502 (1990); Wagner et al., *Pharmacopsychiatry* 21: 301 (1988); Pomerleau et al., *Addictive Behaviors* 9: 265 (1984); Onaivi et al., *Life Sci.* 54 (3): 193 (1994) and Hamon, *Trends in Pharmacol. Res.* 15: 36.

Various nicotinic compounds have been reported as being useful for treating a wide variety of conditions and disorders. See, for example, Williams et al. *DN&P* 7 (4): 205–227 (1994), Arneric et al., *CNS Drug Rev.* 1 (1): 1–26 (1995), Arneric et al., *Exp. Opin. Invest. Drugs* 5 (1): 79–100 (1996), Bencherif et al., *JPET* 279: 1413 (1996), Lippiello et al., *JPET* 279: 1422 (1996), PCT WO 94/08992, PCT WO 96/31475, and U.S. Pat. Nos. 5,583,140 to Bencherif et al., 5,597,919 to Dull et al., and 5,604,231 to Smith et al. Nicotinic compounds are particularly useful for treating a wide variety of Central Nervous System (CNS) disorders.

CNS disorders are a type of neurological disorder. CNS disorders can be drug induced; can be attributed to genetic predisposition, infection or trauma; or can be of unknown etiology. CNS disorders comprise neuropsychiatric disorders, neurological diseases and mental illnesses; and include neurodegenerative diseases, behavioral disorders, cognitive disorders and cognitive affective disorders. There are several CNS disorders whose clinical manifestations have been attributed to CNS dysfunction (i.e., disorders resulting from inappropriate levels of neurotransmitter release, inappropriate properties of neurotransmitter receptors, and/or inappropriate interaction between neurotransmitters and neurotransmitter receptors). Several CNS disorders can be attributed to a cholinergic deficiency, a dopaminergic deficiency, an adrenergic deficiency and/or a serotonergic deficiency. CNS disorders of relatively common occurrence include presenile dementia (early onset Alzheimer's disease), senile dementia (dementia of the Alzheimer's type), Parkinsonism including Parkinson's disease, Huntington's chorea, tardive dyskinesia, hyperkinesia, mania, attention deficit disorder, anxiety, dyslexia, schizophrenia and Tourette's syndrome.

Senile dementia of the Alzheimer's type (SDAT) is a debilitating neurodegenerative disease, mainly afflicting the elderly; characterized by a progressive intellectual and personality decline, as well as a loss of memory, perception, reasoning, orientation and judgment. One feature of the disease is an observed decline in the function of cholinergic systems, and specifically, a severe depletion of cholinergic neurons (i.e., neurons that release acetylcholine, which is believed to be a neurotransmitter involved in learning and memory mechanisms). See, Jones, et al., *Intern. J. Neurosci.* 50: 147 (1990); Perry, *Br. Med. Bull.* 42: 63 (1986); and Sitaram, et al., *Science* 201: 274 (1978). It has been observed that nicotinic acetylcholine receptors, which bind nicotine and other nicotinic agonists with high affinity, are depleted during the progression of SDAT. See, Giacobini, *J. Neurosci. Res.* 27: 548 (1990); and Baron, *Neurology* 36: 1490 (1986). As such, it would seem desirable to provide therapeutic compounds which either directly activate nicotinic receptors in place of acetylcholine or act to minimize the loss of those nicotinic receptors.

Certain attempts have been made to treat SDAT. For example, nicotine has been suggested to possess an ability to activate nicotinic cholinergic receptors upon acute administration, and to elicit an increase in the number of such receptors upon chronic administration to animals. See, Rowell, *Adv. Behav. Biol.* 31: 191 (1987); and Marks, *J. Pharmacol. Exp. Ther.* 226: 817 (1983). It also has been proposed that nicotine can act directly to elicit the release of acetylcholine in brain tissue, to improve cognitive functions, and to enhance attention. See, Rowell, et al., *J. Neurochem.* 43: 1593 (1984); Sherwood, *Human Psychopharm.* 8: 155 (1993); Hodges, et al., *Bio. of Nic.* Edit. by Lippiello, et al., p. 157 (1991); Sahakian, et al., *Br. J. Psych.* 154: 797 (1989); and U.S. Pat. Nos. 4,965,074 to Leeson and 5,242,935 to Lippiello et al. Other methods for treating SDAT have been proposed, including U.S. Pat. Nos. 5,212,188 to Caldwell et al. and 5,227,391 to Caldwell et al., European Patent Application No. 588,917 and PCT WO 96/30372. Another proposed treatment for SDAT is COGNEX®, which is a capsule containing tacrine hydrochloride, available from Parke-Davis Division of Warner-Lambert Company, which reportedly preserves existing acetylcholine levels in patients treated therewith.

Parkinson's disease (PD) is a debilitating neurodegenerative disease, presently of unknown etiology, characterized by tremors and muscular rigidity. A feature of the disease appears to involve the degeneration of dopaminergic neurons (i.e., which secrete dopamine). One symptom of the disease has been observed to be a concomitant loss of nicotinic receptors which are associated with such dopaminergic neurons, and which are believed to modulate the process of dopamine secretion. See, Rinne, et al., *Brain Res.* 54: 167 (1991) and Clark, et al., *Br. J. Pharm.* 85: 827 (1985). It also has been proposed that nicotine can ameliorate the symptoms of PD. See, Smith et al., *Rev. Neurosci.* 3 (1): 25 (1992).

Certain attempts have been made to treat PD. One proposed treatment for PD is SINEMET CR®, which is a sustained-release tablet containing a mixture of carbidopa and levodopa, available from The DuPont Merck Pharmaceutical Co. Another proposed treatment for PD is ELDEPRYL®, which is a tablet containing selefiline hydrochloride, available from Somerset Pharmaceuticals, Inc. Another proposed treatment for PD is PARLODEL®, which is a tablet containing bromocriptine mesylate, available from Sandoz Pharmaceuticals Corporation. Another method for treating PD and a variety of other neurodegenerative diseases has been proposed in U.S. Pat. No. 5,210,076 to Berliner et al.

Tourette's syndrome (TS) is an autosomal dominant neuropsychiatric disorder characterized by a range of neurological and behavioral symptoms. Typical symptoms include (i) the onset of the disorder before the age of 21 years, (ii) multiple motor and phonic tics although not necessarily concurrently, (iii) variance in the clinical phenomenology of the tics, and (iv) occurrence of quasi daily tics throughout a period of time exceeding a year. Motor tics generally include eye blinking, head jerking, shoulder shrugging and facial grimacing; while phonic or vocal tics include throat clearing, sniffling, yelping, tongue clicking and uttering words out of context. The pathophysiology of TS presently is unknown, however it is believed that neurotransmission dysfunction is implicated with the disorder. See, Calderon-Gonzalez et al., *Intern. Pediat.* 8 (2): 176 (1993) and OXFORD TExTBOOK OF MEDICINE, Eds. Weatherall et al., Chapter 21.218 (1987).

It has been proposed that nicotine pharmacology is beneficial in suppressing the symptoms associated with TS. See, Devor et al., *The Lancet* 8670: 1046 (1989); Jarvik, *British J. of Addiction* 86: 571 (1991); McConville et al., *Am. J. Psychiatry* 148 (6): 793 (1991); Newhouse et al., *Brit. J. Addic.* 86: 521 (1991); McConville et al., *Biol. Psychiatry* 31: 832 (1992); and Sanberg et al., *Proceedings from Intl. Symp. Nic.* S39 (1994). It also has been proposed to treat TS using HALDOL®, which is haloperidol available from McNeil Pharmaceutical; CATAPRES®, which is clonidine available from Boehringer Ingelheim Pharmaceuticals, Inc., ORAP®, which is pimozide available from Gate Pharmaceuticals; PROLIXIN®, which is fluphenazine available from Apothecon Division of Bristol-Myers Squibb Co.; and KLONOPIN®, which is clonazepam available from Hoffmann-LaRoche Inc.

Attention deficit disorder (ADD) is a disorder which affects mainly children, although ADD can affect adolescents and adults. See, Vinson, *Arch. Fam. Med.* 3 (5): 445 (1994); Hechtman, *J. Psychiatry Neurosci.* 19 (3): 193 (1994); Faraone et al., *Biol. Psychiatry* 35 (6): 398 (1994) and Malone et al., *J. Child Neurol.* 9 (2): 181 (1994). Subjects suffering from the disorder typically have difficulty concentrating, listening, learning and completing tasks; and are restless, fidgety, impulsive and easily distracted. Attention deficit disorder with hyperactivity (ADHD) includes the symptoms of ADD as well as a high level of activity (e.g., restlessness and movement). Attempts to treat ADD have involved administration of DEXEDRINE®, which is a sustained release capsule containing dextroamphetamine sulfate, available from SmithKline Beecham Pharmaceuticals; RITALIN®, which is a tablet containing methylphenidate hydrochloride, available from Ciba Pharmaceutical Company; and CYLERT®, which is a tablet containing premoline, available from Abbott Laboratories. In addition, it has been reported that administration of nicotine to an individual improves that individual's selective and sustained attention. See, Warburton et al., *CHOLINERGIC CONTROL OF COGNITIVE RESOURCES, EUROPSYCHOBIOLOGY*, Eds. Mendlewicz, et al., pp. 43–46 (1993) and Levin et al. *Psychopharmacology* 123: 55–63 (1996).

Schizophrenia is characterized by psychotic symptoms including delusions, catatonic behavior and prominent hallucinations, and ultimately results in a profound decline in the psychosocial affect of the subject suffering therefrom. Traditionally, schizophrenia has been treated with KLONOPIN®, which is available as a tablet containing clonezepam, available from Hoffmann-LaRoche Inc.; THORAZINE®, which is available as a tablet containing chlorpromazine, available from SmithKline Beecham Pharmaceuticals; and CLORAZIL®, which is a tablet containing clozapine, available from Sandoz Pharmaceuticals. Such neuroleptics are believed to be effective as a result of interaction thereof with the dopaminergic pathways of the CNS. In addition, a dopaminergic dysfunction possessed by individuals suffering from schizophrenia has been proposed. See, Lieberman et al., *Schizophr. Bull.* 19: 371 (1993) and Glassman, *Amer. J. Psychiatry* 150: 546 (1993). Nicotine has been proposed as being effective in effecting neurotransmitter dysfunction associated with schizophrenia. See, Merriam et al., *Psychiatr. Annals* 23: 171 (1993) and Adler et al., *Biol. Psychiatry* 32: 607 (1992). See also Freedman et al., *Proc. Natl. Acad. Sci.* 94: 587–592 (1997).

It would be desirable to provide a useful method for the prevention and treatment of a disorder by administering a nicotinic compound to a patient susceptible to or suffering from such a disorder. It would be highly beneficial to provide individuals suffering from certain disorders (e.g., CNS diseases) with interruption of the symptoms of those disorders by the administration of a pharmaceutical composition containing an active ingredient having nicotinic pharmacology and which has a beneficial effect (e.g., upon the functioning of the CNS), but which does not provide any significant associated side effects (e.g., increased heart rate and blood pressure attendant with interaction of that compound with cardiovascular sites). It would be highly desirable to provide a pharmaceutical composition incorporating a compound which interacts with nicotinic receptors, such as those which have the potential to affect the functioning of the CNS, but which compound does not significantly affect those receptors which have the potential to induce undesirable side effects (e.g., appreciable pressor cardiovascular effects and appreciable activity at skeletal muscle sites).

SUMMARY OF THE INVENTION

The present invention relates to aryl substituted olefinic amine compounds. Such compounmds are useful for providing prevention or treatment of central nervous system (CNS) disorders.

In another aspect, the present invention relates to pharmaceutical compositions comprising effective amounts of compounds of the present invention. The pharmaceutical compositions of the present invention each include a compound which is capable of interacting with nicotinic receptor sites of a patient, and thereby acting as a therapeutic agent in the prevention or treatment of a CNS disorder.

In another aspect, the present invention relates to a method for providing prevention or treatment of central nervous system (CNS) disorders. In particular, the method involves administering an aryl substituted olefinic amine compound according to the present invention.

The pharmaceutical compositions of the present invention are useful for the prevention and treatment of CNS disorders. The pharmaceutical compositions provide therapeutic benefit to individuals suffering from certain CNS disorders and exhibiting clinical manifestations of such disorders in that the compounds within those compositions have the potential to (i) exhibit nicotinic pharmacology and affect nicotinic receptors sites in the CNS (e.g., act as a pharmacological agonist to activate nicotinic receptors), and (ii) elicit neurotransmitter secretion, and hence prevent and suppress the symptoms associated with those diseases. In addition, the compounds are expected to have the potential to (i) increase the number of nicotinic cholinergic receptors of the brain of the patient, (ii) exhibit neuroprotective effects and (iii) not provide appreciable adverse side effects (e.g., significant increases in blood pressure and heart rate, and significant effects upon skeletal muscle). The pharmaceutical compositions of the present invention are believed to be safe and effective with regards to prevention and treatment of CNS disorders.

DETAILED DESCRIPTION OF THE INVENTION

The compounds of the present invention include compounds of the formula I:

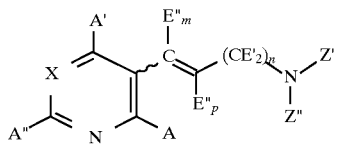

where X is nitrogen or carbon bonded to a substituent species characterized as having a sigma m value greater than 0, often greater than 0.1, and generally greating than 0.2, and even greater than 0.3; less than 0 and generally less than −0.1; or 0; as determined in accordance with Hansch et al., Chem. Rev. 91: 165 (1991); n is an integer which is 1, 2, 3, 4, 5, 6, 7, or 8, preferably is 1, 2, or 3, and most preferably is 2 or 3; E' represents hydrogen or lower alkyl (e.g., straight chain or branched alkyl including $C_1$–$C_8$, preferably $C_1$–$C_5$, such as methyl, ethyl, or isopropyl) or halo substituted lower alkyl (e.g., straight chain or branched alkyl including $C_1$–$C_8$, preferably $C_1$–$C_5$, such as trifluoromethyl or trichloromethyl), but preferably is H; E" represents lower alkyl (e.g., straight chain or branched alkyl including $C_1$–$C_8$, preferably $C_1$–$C_5$, such as methyl, ethyl, or isopropyl) or halo substituted lower alkyl (e.g., straight chain or branched alkyl including $C_1$–$C_8$, preferably $C_1$–$C_5$, such as trifluoromethyl or trichloromethyl); Z' and Z" individually represent hydrogen or lower alkyl (e.g., straight chain or branched alkyl including $C_1$–$C_8$, preferably $C_1$–$C_5$, such as methyl, ethyl, or isopropyl), and preferably at least one of Z' and Z" is hydrogen, and most preferably Z' is hydrogen and Z" is methyl; alternatively Z' is hydrogen and Z" represents a ring structure (cycloalkyl or aromatic), such as cyclopropyl, cyclobutyl, cyclopentyl, cyclohexyl, cycloheptyl, adamantyl, quinuclidinyl, pyridinyl, quinolinyl, pyrimidinyl, phenyl, benzyl (where any of the foregoing can be suitably substiuted with at least one substituent group, such as alkyl, halo, or amino substituents); alternatively Z', Z", and the associated nitrogen atom can form a ring structure such as aziridinyl, azetidinyl, pyrollidinyl, piperidinyl, piperazinyl, or morpholinyl; A, A' and A" individually represent hydrogen, halo (e.g., F, Cl, Br, or I), alkyl (e.g., lower straight chain or branched $C_{1-8}$ alkyl, but preferably methyl or ethyl), or NX"X'" where X" and X'" are individually hydrogen or lower alkyl, including $C_1$–$C_8$, preferably $C_1$–$C_5$ alkyl; m is 0 or 1, preferably 0; p is 0 or 1, preferably 0; the wavy line in the structure represents a cis (Z) or trans (E) form of the compound. When m or p is 0, E" is not present and H fills the valence of the carbon on which E" is positioned. More specifically, X includes N, C—H, C—F, C—Cl, C—Br, C—I, C—R', C—NR'R", C—CF$_3$, C—OH, C—CN, C—NO$_2$, C—C$_2$R', C—SH, C—SCH$_3$, C—N$_3$, C—SO$_2$CH$_3$, C—OR', C—SR', C—C(=O)NR'R", C—NR'C(=O)R', C—C(=O)R', C—C(=O)OR', C(CH$_2$)$_q$OR', C—OC(=O)R', COC(=O)NR'R" and C—NR'C(=O)OR' where R' and R" are individually hydrogen or lower alkyl (e.g., $C_1$–$C_{10}$ alkyl, preferably $C_1$–$C_5$ alkyl, and more preferably methyl, ethyl, isopropyl or isobutyl), an aromatic group-containing species or a substituted aromatic group-containing species, and q is an integer from 1 to 6. R' and R" can be straight chain or branched alkyl, or R' and R" can form a cycloalkyl funtionality (e.g., cyclopropyl cyclobutyl, cyclopentyl, cyclohexyl, cycloheptyl, adamantyl, and quinuclidinyl). Representative aromatic group-containing species include pyridinyl, quinolinyl, pyrimidinyl, phenyl, and benzyl (where any of the foregoing can be suitably substituted with at least one substituent group, such as alkyl, halo, or amino substituents). Other representative aromatic ring systems are set forth in Gibson et al., J. Med. Chem. 39: 4065 (1996). When X represents a carbon atom bonded to a substituent species, that substituent species often has a sigma m value which is between about −0.3 and about 0.75, and frequently between about −0.25 and about 0.6. In certain circumstances the substituent species is characterized as having a sigma m value not equal to 0. In addition, it is highly preferred that A is hydrogen, it is preferred that A' is hydrogen, and normally A" is hydrogen. Generally, both A and A' are hydrogen; sometimes A and A' are hydrogen, and A" is amino, methyl or ethyl; and often A, A' and A" are all hydrogen. Depending upon the identity and positioning of each individual E', certain compounds can be optically active. Typically, the values of each of m and p, and the selection of E', are such that up to about 4, and frequently up to 3, of the substituents designated as E' and E" are non-hydrogen substituents (i.e., substituents such as lower alkyl or halo-substituted lower alkyl).

Of particularly interest are compounds of Formula I where n, m, p, X, A, A', A", E', E", Z', and Z" are as defined hereinbefore, and those compounds can have the cis (Z) or trans (E) form. For such compounds of particular interest, X most preferably is nitrogen or carbon bonded to a substituent species characterized as having a sigma m value greater than 0, often greater than 0.1, generally greater than 0.2, and even greater than 0.3; less than 0 and generally less than −0.1; or 0. More specifically, the compounds of particular interest are those compounds wherein X is CH, C—Br, C(CH$_2$)$_q$OR', where R' is an aromatic ring, particularly phenyl; C—O—R' where R' is an aromatic ring, particularly phenyl; C—O—R' where R' is an alkyl particularly isopropyl or ethyl; C—COR' where R' is methyl.

One representative compound is (E)-N-methyl-4-[3-(5-benzyloxypyridin)yl]-3-buten-1-amine for which X is C—O—CH$_2$Ar, where Ar is phenyl, E' is H, n is 2, m is 0, p is 0, A, A', A", and Z' are each H, and Z" is methyl. Another representative compound is (E)-4-[3-(5-bromopyrdin)yl]-3-buten-1-amine for which X is C—Br, E' is H, n is 2, m is 0, p is 0, and A, A', A", Z' and Z" are each H. Another representative compound is (E)-N-methyl-4-[3-(5-phenoxypyridin)yl]-3-buten-1-amine for which X is C—O—Ar where Ar is phenyl, E' is H, n is 2, m is 0, p is 0, A, A', A", and Z' are each H, and Z" is methyl. Another representative compound is (E)-N-methyl-4-[3-(5-isopropoxypyridin)yl]-3-buten-1-amine for which X is C—O—R' where R' is isopropyl, E' is H, n is 2, m is 0, p is 0, A, A', A", and Z' are each H, and Z" is methyl. Another representative compound is (E)-N-methyl-4-[3-(5-methoxymethylpyridin)yl-3-buten-1-amine for which X is C—$CH_2$—O—$CH_3$, E' is H, n is 2, m is 0, p is 0, A, A', A", and Z' are each H, and Z" is methyl. Another representative compound is (E)-N-methyl-4-[3-(5-phenylpyridin)yl]-3-buten-1-amine for which X is C—R' where R' is phenyl, E' is H, n is 2, E" is H, m is 0, p is 0, A, A', A", and Z' are each H, and Z" is methyl. Another representative compound is (E)-4-(3-pyridinyl)-3-buten-1-amine for which X is $CH_2$, E' is H, n is 2, m is 0, p is 0, and A, A', A", Z' and Z" are each H. Another representative compound is (E)-N-methyl-4-[3-(5-ethoxypyridin)yl]-3-buten-1-amine for which X is C—O—R' where R' is ethyl, E' is H, n is 2, m is 0, p is 0, A, A', A", Z' are each H, and Z" is methyl.

Another representative compound is (E)-N-methyl-4-[3-5-(ethylthiopyridinyl)]-3-buten-1-amine for which X is C—S—$C_2H_5$, E' is H, n is 2, m is 0, p is 0, and A, A', A" and Z' are each H and Z" is methyl. Another representative compound is (E)-N-methyl-4-[3-5-acetamidopyridinyl]-3-buten-1-amine for which X is C—NH—C(=O)—$CH_3$, E' is H, n is 2, m is 0, p is 0, and A, A', A" and Z' are each H and Z" is methyl. Another representative compound is (E)-N-methyl-4-[3-5-carbamoyl-pyridinyl]-3-buten-1-amine for which X is C—C(=O)—$NH_2$, E' is H, n is 2, m is 0, p is 0, and A, A', A" and Z' are each H and Z" is methyl.

The manner in which aryl substituted olefinic amine compounds of the present invention are provided can vary. (E)-metanicotine can be prepared using the techniques set forth by Loffler et al., *Chem. Ber.* 42: 3431 (1909) and Laforge, *J.A.C.S.* 50: 2477 (1928). Certain novel 6-substituted metanicotine-type compounds can be prepared from the corresponding 6-substituted nicotine-type compounds using the general methods of Acheson et al., *J. Chem. Soc., Perkin Trans.* 1 2: 579 (1980). The requisite precursors for such compounds, i.e., 6-substituted nicotine-type compounds, can be synthesized from 6-substituted nicotinic acid esters using the general methods disclosed by Rondahl, *Acta Pharm. Suec.* 14: 113 (1977). Preparation of certain 5-substituted metanicotine-type compounds can be accomplished from the corresponding 5-substituted nicotine-type compounds using the general method taught by Acheson et al., *J. Chem. Soc., Perkin Trans.* 1 2: 579 (1980). The 5-halo nicotine-type compounds and the 5-amino nicotine-type compounds can be prepared using the general procedures disclosed by Rondahl, *Act. Pharm. Suec.* 14: 113 (1977). The 5-trifluoromethyl nicotine-type compounds can be prepared using the techniques and materials set forth in Ashimori et al., *Chem. Pharm. Bull.* 38 (9): 2446 (1990) and Rondahl, *Acta Pharm. Suec.* 14: 113 (1977). Certain metanicotine-type compounds (e.g., 3-(5-phenylpyridin)yl-3-alkene-amine type compounds) can be prepared using the types of synthetic methodologies set forth in Miyaura et al., *Synth. Commun.* 11: 513 (1981) and U.S. Pat. No. 5,409,920 to Guthikonda et al. Furthermore, preparation of certain metanicotine-type compounds can be accomplished using a palladium catalyzed coupling reaction of an aromatic halide and a terminal olefin containing a protected amine substituent, removal of the protective group to obtain a primary amine, and optional alkylation to provide a secondary or tertiary amine. In particular, certain metanicotine-type compounds can be prepared by subjecting a 3-halo substituted, 5-substituted pyridine compound or a 5-halo substituted pyrimidine compound to a palladium catalyzed coupling reaction using an olefin possessing a protected amine functionality (e.g., an olefin provided by the reaction of a phthalimide salt with 3-halo-1-propene, 4-halo-1-butene, 5-halo-1-pentene or 6-halo-1-hexene). See, Frank et al., *J. Org. Chem.* 43 (15): 2947 (1978) and Malek et al., *J. Org. Chem.* 47: 5395 (1982). Alternatively, certain metanicotine-type compounds can be prepared by coupling an N-protected, modified amino acid residue, such as 4-(N-methyl-N-tert-butyloxycarbonyl)amino-butyric acid methyl ester, with an aryl lithium compound, as can be derived from a suitable aryl halide and butyl lithium. The resulting N-protected aryl ketone is then chemically reduced to the corresponding alcohol, converted to the alkyl halide, and subsequently dehydrohalogenated to introduce the olefin functionality. Removal of the N-protecting group affords the desired metanicotine-type compound.

There are a number of different methods for providing (Z)-metanicotine-type compounds. In one method, (Z)-metanicotine-type compounds can be synthesized from nicotine as a mixture of the E and Z isomers; and the (Z)-metanicotine-type compounds can then be separated by chromatography using the types of techniques disclosed by Sprouse et al., Abstracts of Papers, p. 32, Coresta/TCRC Joint Conference (1972). In another method, (Z)-metanicotine can be prepared by the controlled hydrogenation of the corresponding acetylenic compound (e.g., N-methyl-4-(3-pyridinyl)-3-butynylamine). For example, certain 5-substituted (Z)-metanicotine-type compounds and certain 6-substituted (Z)-metanicotine-type compounds can be prepared from 5-substituted-3-pyridinecarboxaldehydes and 6-substituted-3-pyridinecarboxaldehydes, respectively.

Representative compounds of the present invention, representative starting materials, and methods of synthesizing representative compounds and suitable salts thereof are set forth in U.S. Pat. No. 5,597,919 to Dull et al.; U.S. patent application Ser. No. 08/631,762; U.S. patent application Ser. No. 08/635,165; and PCT No. WO 96/31475.

One representative compound, (E)-N-methyl-4-(3-[5-(ethylthio)pyridinyl])-3-buten-1-amine is prepared from N-methyl-N-(tert-butoxycarbonyl)-3-buten-1-amine and 3-bromo-5-(ethylthio)pyridine using the techniques set forth in W. C. Frank, et al., *J. Org. Chem.* 43 (15): 2947 (1978), and the tert-butoxy carbonyl protecting group is subsequently removed. Specifically, N-methyl-N-(tert-butoxycarbonyl)-3-buten-1-amine is prepared by (i) reacting 4-bromo-1-butene at 0.035 mole scale with a ten fold excess of condensed methylamine in N,N-dimethylformamide solvent in the presence of potassium carbonate to provide a 97% yield of N-mehtyl-3-buten-1-amine; (ii) the amine thus prepared is reacted at 0.030 mole scale with one equivalent of di-tert-butyldicarbonate in tetrahydrofuran to give N-methyl-N-(tert-butoxycarbonyl)-3-buten-1-amine in 68% yield. The 3-bromo-5-(ethylthio)pyridine is produced by the reaction of sodium ethanethiolate on 3,5-dibromopyridine in N,N-dimethylformamide in 86% yield. N-methyl-N-(tert-butoxycarbonyl)-3-buten-1-amine and 3-bromo-5-(ethylthio)pyridine are reacted using the Heck reaction on a 1.6 mmole scale in 2:1 acetonitrile:triethylamine using a catalyst consistingof one mole percent palladium acetate and four mole percent tri-o-tolylphosphine. N-methyl-N-(tert-butoxycarbonyl)-4-(3-[5-(ethylthio)pyridinyl])-3-buten-1-amine is obtained in 59% yield. Deprotection of the product may then be accomplished by 1:1 6N hydrochloric acid:tetrahdyrofuran.

Other representative compounds include (E)-N-methyl-4-[3-(5-acetamidopyridinyl)]-3-buten-1-amine and (E)-N-methyl-4-[3-(5-carbamoylpyridinyl)]-3-buten-1-amine. These compounds may be produced according to the techniques set forth in C. V. Greco et al., *J. Heterocyclic Chem.* 7 (4): 761 (1970). More specifically, the commercially available starting material, 5-bromonicotinic acid is converted to both 5-bromonicotinamide and 3-amino-5-bromopyridine. The 3-amino-5-bromopyridine can be acylated with acetic anhydride to give 3-acetamido-5-bromopyridine. 3-Acetamido-5-bromopyridine may then be reacted with N-methyl-N-(tert-butoxycarbonyl)-3-buten-1-amine (prepared according to the preceeding techniques) using the Heck reaction described hereinabove and set forth in W. C. Frank et al., *J. Org. Chem.* 43 (15): 2947 (1978). The reaction gives (E)-N-methyl-N-(tert-butoxycarbonyl)-4-[3-(5-acetamidopyridinyl)]-3-buten-1-amine. The Heck reaction of 5-bromonicotinic acid with N-methyl-N-(tert-butoxycarbonyl)-3-buten-1-amine gives (E)-N-methyl-N-(tert-butoxycarbonyl)-4-[3-(5-carbamoylpyridinyl)]-3-buten-1-amine. The treatment of either product with aqueous acid effects the removal of the tert-butoxycarbonyl groups from these compounds, giving the 5-acetamido and 5-carbamoyl substituted metanicotinic compounds respectively.

The present invention relates to a method for providing prevention of a CNS disorder to a subject susceptible to such a disorder, and for providing treatment to a subject suffering from a CNS disorder. In particular, the method comprises administering to a patient an amount of a compound effective for providing some degree of prevention of the progression of the CNS disorder (i.e., provide protective effects), amelioration of the symptoms of the CNS disorder, and amelioration of the reoccurrence of the CNS disorder. The method involves administering an effective amount of a compound selected from the general formulae which are set forth hereinbefore. The present invention relates to a pharmaceutical composition incorporating a compound selected from the general formulae which are set forth hereinbefore. The compounds normally are not optically active. However, certain compounds can possess substituent groups of a character so that those compounds possess optical activity. Optically active compounds can be employed as racemic mixtures or as enantiomers. The compounds can be employed in a free base form or in a salt form (e.g., as pharmaceutically acceptable salts). Examples of suitable pharmaceutically acceptable salts include inorganic acid addition salts such as hydrochloride, hydrobromide, sulfate, phosphate, and nitrate; organic acid addition salts such as acetate, propionate, succinate, lactate, glycolate, malate, tartrate, citrate, maleate, fumarate, methanesulfonate, p-toluenesulfonate, and ascorbate; salts with acidic amino acid such as aspartate and glutamate; alkali metal salts such as sodium salt and potassium salt; alkaline earth metal salts such as magnesium salt and calcium salt; ammonium salt; organic basic salts such as trimethylamine salt, triethylamine salt, pyridine salt, picoline salt, dicyclohexylamine salt, and N,N'-dibenzylethylenediamine salt; and salts with basic amino acid such as lysine salt and arginine salt. The salts may be in some cases hydrates or ethanol solvates.

CNS disorders which can be treated in accordance with the present invention include presenile dementia (early onset Alzheimer's disease), senile dementia (dementia of the Alzheimer's type), Parkinsonism including Parkinson's disease, Huntington's chorea, tardive dyskinesia, hyperkinesia, mania, attention deficit disorder, anxiety, dyslexia, schizophrenia and Tourette's syndrome.

The pharmaceutical composition also can include various other components as additives or adjuncts. Exemplary pharmaceutically acceptable components or adjuncts which are employed in relevant circumstances include antioxidants, free radical scavenging agents, peptides, growth factors, antibiotics, bacteriostatic agents, immunosuppressives, anticoagulants, buffering agents, anti-inflammatory agents, anti-pyretics, time release binders, anaesthetics, steroids and corticosteroids. Such components can provide additional therapeutic benefit, act to affect the therapeutic action of the pharmaceutical composition, or act towards preventing any potential side effects which may be posed as a result of administration of the pharmaceutical composition. In certain circumstances, a compound of the present invention can be employed as part of a pharmaceutical composition with other compounds intended to prevent or treat a particular CNS disorder.

The manner in which the compounds are administered can vary. The compounds can be administered by inhalation (e.g., in the form of an aerosol either nasally or using delivery articles of the type set forth in U.S. Pat. No. 4,922,901 to Brooks et al.); topically (e.g., in lotion form); orally (e.g., in liquid form within a solvent such as an aqueous or non-aqueous liquid, or within a solid carrier); intravenously (e.g., within a dextrose or saline solution); as an infusion or injection (e.g., as a suspension or as an emulsion in a pharmaceutically acceptable liquid or mixture of liquids); or transdermally (e.g., using a transdermal patch). Although it is possible to administer the compounds in the form of a bulk active chemical, it is preferred to present each compound in the form of a pharmaceutical composition or formulation for efficient and effective administration. Exemplary methods for administering such compounds will be apparent to the skilled artisan. For example, the compounds can be administered in the form of a tablet, a hard gelatin capsule or as a time release capsule. As another example, the compounds can be delivered transdermally using the types of patch technologies available from Ciba-Geigy Corporation and Alza Corporation. The administration of the pharmaceutical compositions of the present invention can be intermittent, or at a gradual, continuous, constant or controlled rate to a warm-blooded animal, such as a human being. In addition, the time of day and the number of times per day that the pharmaceutical formulation is administered can vary. Administration preferably is such that the active ingredients of the pharmaceutical formulation interact with receptor sites within the body of the subject that effect the functioning of the CNS.

The dose of the compound is that amount effective to prevent occurrence of the symptoms of the condition being prevented, or to treat some symptoms of the condition from which the patient suffers. By "effective amount", "therapeutic amount" or "effective dose" is meant an amount sufficient to elicit the desired pharmacological or therapeutic effects, thus resulting in effective prevention or treatment of the CNS disorder. Thus, an effective amount of compound is an amount sufficient to pass across the blood-brain barrier of the subject, to bind to relevant receptor sites in the brain of the subject, and to elicit neuropharmacological effects (e.g., elicit neurotransmitter secretion, thus resulting in effective prevention or treatment of the disorder). Prevention of the disorder is manifested by a prolonging or delaying of the onset of the symptoms of the condition. Treatment of the condition is manifested by a decrease in the symptoms associated with the disorder or an amelioration of the reoccurrence of the symptoms of the disorder.

The effective dose can vary, depending upon factors such as the condition of the patient, the severity of the symptoms experienced by the patient, and the manner in which the pharmaceutical composition is administered. For human patients, the effective dose of typical compounds generally requires administering the compound in an amount of at least about 1, often at least about 10, and frequently at least about 25 mg/24 hr./patient. For human patients, the effective dose of typical compounds requires administering the compound which generally does not exceed about 500, often does not exceed about 400, and frequently does not exceed about 300 mg/24 hr./patient. In addition, administration of the effective dose is such that the concentration of the compound within the plasma of the patient normally does not exceed 500 ng/ml, and frequently does not exceed 100 ng/ml.

The compounds useful according to the method of the present invention have the ability to pass across the blood-brain barrier of the patient. As such, such compounds have the ability to enter the central nervous system of the patient. The log P values of typical compounds useful in carrying out the present invention generally are greater than −0.5, often are greater than about 0, and frequently are greater than about 0.5. The log P values of such typical compounds generally are less than about 3.5, often are less than about 3.0, and frequently are less than about 2.5. Log P values provide a measure of the ability of a compound to pass across a diffusion barrier, such as a biological membrane. See, Hansch, et al., *J. Med. Chem.* 11: 1 (1968).

The compounds useful according to the method of the present invention have the ability to interact with certain nicotinic cholinergic receptors in the brain of the patient. As such these compound have the ability to express nicotinic pharmacology, and in particular, to act as nicotinic agonists. The receptor binding constants of typical compounds useful in carrying out the present invention generally exceed about 1 nM, often exceed about 5 nM, and frequently exceed about 10 nM. The receptor binding constants of such typical compounds generally are less than about 1000 nM, often are less than about 500 nM, frequently are less than about 200 nM, and even less than 100 nM. Receptor binding constants provide a measure of the ability of the compound to bind to relevant receptor sites of certain cells of the patient. See, Cheng, et al., *Biochem. Pharmacol.* 22: 3099 (1973).

The compounds useful according to the method of the present invention have the ability to demonstrate a nicotinic pharmacology by effectively eliciting neurotransmitter secretion from nerve ending preparations (i.e., synaptosomes). As such, these compounds have the ability to cause relevant neurons to release or secrete acetylcholine, dopamine, and other neurotransmitters. Generally, the compounds useful in carrying out the present invention provide for the secretion of dopamine in amounts of at least about 10 percent, often at least about 25 percent, frequently at least about 50 percent and even greater than 75 percent, of that elicited by an equal molar amount of (S)-(−)-nicotine. Certain compounds of the present invention can provide secretion of dopamine in an amount which can exceed that elicited by an equal molar amount of (S)-(−)-nicotine.

The compounds of the present invention, when employed in effective amounts in accordance with the method of the present invention, lack the ability to elicit activation of nicotinic receptors of human muscle to any significant degree. In that regard, the compounds of the present invention demonstrate poor ability to cause isotopic rubidium ion flux through nicotinic receptors in cell preparations derived from muscle preparations. Thus, such compounds exhibit receptor activation constants or EC50 values (i.e., which provide a measure of the concentration of compound needed to activate half of the relevant receptor sites of the skeletal muscle of a patient) which are relatively high. Generally, typical compounds useful in carrying out the present invention activate isotopic rubidium ion flux by less than 20 percent, often by less than 15 percent, and frequently by less than 10 percent, of that elicited by an equal molar amount of (S)-(−)-nicotine.

The compounds of the present invention, when employed in effective amounts in accordance with the method of the present invention, are selective to certain relevant nicotinic receptors, but do not cause significant activation of receptors associated with undesirable side effects. By this is meant that a particular dose of compound resulting in prevention and/or treatment of a CNS disorder is essentially ineffective in eliciting activation of certain ganglionic-type nicotinic receptors. This selectivity of the compounds of the present invention against those receptors responsible for cardiovascular side effects is demonstrated by a lack of the ability of those compounds to activate nicotinic function of adrenal chromaffin tissue. As such, the compounds of the present invention have poor ability to cause isotopic rubidium ion flux through nicotinic receptors in cell preparations derived from the adrenal gland. Generally, the compounds useful in the present invention activate isotopic rubidium ion flux by less than 25 percent, often by less than 15 percent, frequently by less than 10 percent, and even essentially 0 percent, of that elicited by an equal molar amount of (S)-(−)-nicotine.

Compounds of the present invention, when employed in effective amounts in accordance with the method of the present invention, are effective towards providing some degree of prevention of CNS disorders amelioration of the symptoms of such disorders, and amelioration to some degree of the reoccurrence of such disorders. However, such effective amounts of those compounds are not sufficient to elicit any appreciable side effects, as demonstrated by increased effects relating to the cardiovascular system, and effects to skeletal muscle. As such, administration of compounds of the present invention provides a therapeutic window in which treatment of CNS disorders is provided, and side effects are avoided. That is, an effective dose of a compound of the present invention is sufficient to provide the desired effects upon the CNS, but is insufficient (i.e., is not at a high enough level) to provide undesirable side effects. Preferably, effective administration of a compound of the present invention resulting in treatment of a CNS disorder occurs upon administration of less than 1/5, often less than 1/10, and frequently less than 1/15, that amount sufficient to cause any side effects to a significant degree.

The following examples are provided to illustrate the present invention, and should not be construed as limiting thereof. In these examples, all parts and percentages are by weight, unless otherwise noted.

EXAMPLE 1

Sample No. 1 is (E)-N-Methyl-4-[3-(5-benzyloxypyridin)yl]-3-buten-1-amine, which was prepared according to the following procedure.

3-Bromo-5-benzyloxypyridine: Under a nitrogen atmosphere, small pieces of sodium (1.48 g, 64.4 mmol) were added to benzyl alcohol (17.11 g, 158.0 mmol), and the mixture was stirred and heated at 70° C. for 18 h. To the stirring, viscous mixture was added 3,5-dibromopyridine (5.00 g, 21.1 mmol), copper powder (255 mg, 4.0 mmol), and benzyl alcohol (15 mL). The mixture was further heated at 100° C. for 48 h. The reaction mixture was allowed to cool to ambient temperature, diluted with water (50 mL), and extracted with diethyl ether (5×50 mL). The combined ether extracts were dried ($Na_2SO_4$), filtered, and concentrated by rotary evaporation. Vacuum distillation removed excess benzyl alcohol, bp 68°–72° C. at 2.6 mm Hg. Further vacuum distillation afforded 3.17 g (38.0%) of 3-bromo-5-benzyloxypyridine as a white, crystalline solid, mp 64°–66° C.

$^1$H NMR ($CDCl_3$, 300 MHz): δ 8.28 (2H, m), 7.42–7.34 (6H, m), 5.08 (2H, s).

$^{13}$C NMR (CDCl$_3$, 75 MHz): δ 155.20, 143.21, 136.71, 135.44, 128.79, 128.55, 127.55, 126.97, 124.37, 70.65.

HRMS: Calcd. for C$_{12}$H$_{10}$BrNO (M$^+$): m/z 262.994575. Found: 262.995321.

(E)-4-[3-(5-Benzyloxypyridin)yl]-3-buten-1-ol: Under a nitrogen atmosphere, a mixture of 3-buten-1-ol (151 mg, 2.1 mmol), 3-bromo-5-benzyloxypyridine (528 mg, 2.0 mmol), palladium(II) acetate (5 mg, 0.02 mmol), tri-o-tolylphosphine (25 mg, 0.08 mmol), triethylamine (0.5 mL), and acetonitrile (1.0 mL) was stirred and heated under reflux for 20 h. Upon cooling, the mixture was diluted with water (10 mL) and extracted with dichloromethane (2×10 mL). The combined dichloromethane extracts were dried (Na$_2$SO$_4$), filtered, and concentrated by rotary evaporation to give a dark-yellow oil (527 mg). Purification by column chromatography on silica gel, eluting with 2.5% (v/v) methanol in ethyl acetate afforded 387 mg (75.8%) of (E)-4-[3-(5-benzyloxypyridin)yl]-3-buten-1-ol as a colorless gum.

$^1$H NMR (CDCl$_3$, 300 MHz): δ 8.21 (1H, d, J=2.7 Hz), 8.18 (1H, d, J=1.6 Hz), 7.41–7.33 (5H, m), 7.25 (1H, s), 6.44 (1H, d, J=15.9 Hz), 6.27 (1H, dt, J=16.0, 7.0 Hz), 5.09 (2H, s), 3.77 (2H, t, J=6.2 Hz), 2.44 (2H, dq, J=6.2, 1.0 Hz), 1.67 (1H, br s).

(E)-N-Methyl-4-[3-(5-benzyloxypyridin)yl]-3-buten-1-amine: Under a nitrogen atmosphere, a cold (0° C.), stirring solution of (E)-4-[3-(5-benzyloxypyridin)yl]-3-buten-1-ol (368 mg, 1.44 mmol), dichloromethane (1.5 mL), and pyridine (1 drop) was treated with p-toluenesulfonyl chloride (302 mg, 1.58 mmol). The mixture was allowed to warm to ambient temperature. After stirring for 16 h, the solution was concentrated under a stream of nitrogen, and the residue was further dried under high vacuum. The resulting residue was dissolved in tetrahydrofuran (3 mL), and 40% aqueous methylamine (3 mL) was added. The solution was stirred 6 h at ambient temperature and was then concentrated by rotary evaporation to a dark gum. The residue was partitioned between 1M NaOH solution (10 mL) and chloroform (10 mL). The chloroform layer was separated, washed with water (10 mL), dried (Na$_2$SO$_4$), filtered, and concentrated by rotary evaporation to give a dark-brown oil (445 mg). The product was purified by column chromatography on silica gel, eluting with 2.5% (v/v) triethylamine in methanol to give 162 mg (41.9%) of (E)-N-methyl-4-[3-(5-benzyloxypyridin)yl]-3-buten-1-amine as a light-yellow oil.

$^1$H NMR (CDCl$_3$, 300 MHz): δ 8.20 (1H, d, J=2.7 Hz), 8.17 (1H, d, J=1.8 Hz), 7.43–7.33 (5H, m), 7.22 (1H, m), 6.40 (1H, d, J=15.9 Hz), 6.24 (1H, dt, J=15.9, 6.9 Hz), 5.09 (2H, s), 2.72 (2H, t, J=6.8 Hz), 2.46–2.39 (2H, m), 2.44 (3H, s), 1.76 (1H, br s).

$^{13}$C NMR (CDCl$_3$, 75 MHz): δ 154.92, 140.88, 136.73, 136.17, 133.70, 131.03, 128.71, 128.29, 127.91, 127.53, 117.93, 70.32, 51.03, 36.29, 33.47.

HRMS: Calcd. for C$_{17}$H$_{20}$N$_2$O (M$^+$): m/z 268.157563. Found: 268.157420.

EXAMPLE 2

Sample No. 2 is (E)-4-[3-(5-Bromopyridin)yl]-3-buten-1-amine Hemifumarate, which was prepared according to the following techniques.

N-3-Buten-1-phthalimide was prepared essentially in accordance with the techniques described in W. C. Frank, et al., *J. Org. Chem.* 43: 2947 (1978).

(E)-N-4-[3-(5-Bromopyridin)yl]-3-buten-1-phthalimide: Under a nitrogen atmosphere, a mixture of N-3-buten-1-phthalimide (8.74 g, 43.5 mmol), 3,5-dibromopyridine (10.00 g, 42.2 mmol), palladium(II) acetate (190 mg, 0.84 mmol), tri-o-tolylphosphine (514 mg, 1.69 mmol), and triethylamine (8.55 g, 84.4 mmol) was stirred at 100°–107° C. (oil bath temperature) for 48 h. Upon cooling to ambient temperature, the brown residue was filtered, washed with water (200 mL), and dissolved in hot N,N-dimethylformamide (45 mL). The resulting solution was filtered through Celite® filter aid. Water (50 mL) was added to the filtrate, and the mixture was cooled at 5° C. for 18 h. The resulting solids were filtered, washed with cold water, followed by cold 2-propanol (10 mL), and vacuum dried at 50° C. to give a yellowish brown semisolid (13.69 g). The product was recrystallized twice from toluene (40 mL), filtered, washed with cold toluene (5 mL) and cold 2-propanol (5 mL), and vacuum dried at 50° C. to give 2.11 g (14.0%) of (E)-N-4-[3-(5-bromopyridin)yl]-3-buten-1-phthalimide as a light beige powder, mp 145°–148° C.

$^1$H NMR (CDCl$_3$): δ 8.46 (1H, d, J=2.0 Hz), 8.37 (1H, d, J=1.8 Hz), 7.82 (2H, m), 7.74 (1H, t, J=2.0 Hz), 7.69 (2H, m), 6.33 (2H, d, J=15.9 Hz), 6.25 (1H, dt, J=15.9, 5.9 Hz), 3.84 (2H, t, J=6.9 Hz), 2.62 (2H, m).

(E)-4-[3-(5-Bromopyridin)yl]-3-buten-1-amine: Under a nitrogen atmosphere, a solution of (E)-N-4-[3-(5-bromopyridin)yl]-3-buten-1-phthalimide (2.16 g, 6.1 mmol), hydrazine hydrate (0.91 g, 18.2 mmol), methanol (40 mL) and chloroform (80 mL) was allowed to stir for 5 h at ambient temperature. The reaction was monitored by thin layer chromatography on silica gel (chloroform-methanol (99:1, v/v)). Additional hydrazine hydrate (0.45 g, 9.1 mmol) was added to the reaction mixture which was stirred at ambient temperature for a total of 45 h. The thick mixture was poured into 1M NaOH solution (750 mL), stirred 30 min at ambient temperature, and extracted with chloroform (3×100, 2×200 mL). The combined chloroform extracts were dried (Na$_2$SO$_4$), filtered, and concentrated by rotary evaporation. Further drying under vacuum at ambient temperature afforded a golden oil (1.11 g). Purification by vacuum distillation produced 0.57 g of a light-yellow oil, bp 109° C. at 0.05 mm Hg. Further purification by vacuum distillation afforded 180 mg (13.1%) of (E)-4-[3-(5-bromopyridin)yl]-3-buten-1-amine as a light-yellow oil, bp 108°–115° C. at 0.03 mm Hg.

$^1$H NMR (CD$_3$OD): δ 8.49 (1H, d, J=1.8 Hz), 8.45 (1H, d, J=2.2 Hz), 8.09 (1H, t, J=2.1 Hz), 6.48 (2H, m), 2.82 (2H, t, J=7.0 Hz), 2.43 (2H, m). EI-MS: m/z (relative intensity) 227 (M$^+$, 0.1%).

(E)-4-[3-(5-Bromopyridin)yl]-3-buten-1-amine Hemifumarate: (E)-4-[3-(5-Bromopyridin)yl]-3-buten-1-amine (173 mg, 0.76 mmol) in a small volume of 2-propanol, was added to a warm solution of fumaric acid (95.6 mg, 0.82 mmol) in 2-propanol. The white mixture was concentrated by rotary evaporation, and the solids were recrystallized from 2-propanol. The mixture was kept at 5° C. for 18 h. The resulting solids were filtered, washed with cold 2-propanol, cold diethyl ether, and dried under vacuum at 50° C. to yield a light-beige powder. A second recrystallization from 2-propanol afforded 103 mg (47.4% yield) of (E)-4-[3-(5-bromopyridin)yl]-3-buten-1-amine hemifumarate as a cream-colored powder, mp 175°–176.5° C.

$^1$H NMR (D$_2$O, 300 MHz): δ 8.51 (1H, s), 8.47 (1H, s), 8.12 (1H, s), 6.59 (1H, d, J=16.0 Hz), 6.51 (1H, s), 6.39 (1H, dt, J=16.0, 7.0 Hz), 3.20 (2H, t, J=7.0 Hz), 2.65 (2H, q, J=7.0 Hz).

$^{13}$C NMR (D$_2$O, 75 MHz): δ 174.62, 148.36, 145.32, 136.50, 135.32, 134.73, 129.24, 128.42, 120.64, 38.67, 30.30.

Analysis calculated for C$_9$H$_{11}$BrN$_2$.0.5 C$_4$H$_4$O$_4$: C, 46.33; H, 4.59; Br, 28.03; N, 9.83. Found: C, 46.20; H, 4.71; Br, 27.92; N, 9.75.

EXAMPLE 3

Sample No. 3 is (E)-N-Methyl-4-[3-(5-phenoxypyridin)yl]-3-buten-1-amine, which was prepared according to the following techniques.

3-Bromo-5-phenoxypyridine: Sodium phenoxide trihydrate (7.50 g, 44.1 mmol) was dried under vacuum at 65° C. for 18 h at 0.6 mm Hg to yield 5.08 g of sodium phenoxide. Under a nitrogen atmosphere, 3,5-dibromopyridine (4.00 g, 16.9 mmol) and anhydrous N,N-dimethylformamide (40 mL) were added to the sodium phenoxide (5.08 g, 43.8 mmol). The resulting mixture was stirred at 110° C. for 44 h. After cooling to ambient temperature, water (75 mL) was added, and the pH was adjusted to 13.0 using 30% NaOH solution. The solution was extracted with diethyl ether (4×60 mL). The combined ether extracts were washed with saturated NaCl solution (50 mL), dried (NaSO$_4$), filtered and concentrated by rotary evaporation to a brown oil (4.0 g). The oil was vacuum distilled, collecting a forerun (317 mg), bp 48°–65° C. at 0.05 mm Hg. Further distillation afforded 3.35 g (79.8%) of 3-bromo-5-phenoxypyridine as a pale-yellow oil, bp 75°–112° C. at 0.05 mm Hg (lit. bp 110°–115° C. at 1.7 mm Hg, see K. Fujikawa, et al. *Agr. Biol. Chem.* 34: 68 (1970).

$^1$H NMR (CDCl$_3$, 300 MHz): δ 8.39 (1H, d, J=1.7 Hz), 8.31 (1H, d, J=2.3 Hz), 7.42–7.35 (3H, m), 7.22–7.17 (1H, m), 7.05–7.01 (2H, m).

(E)-4-[3-(5-Phenoxypyridin)yl]-3-buten-1-ol: Under a nitrogen atmosphere, a mixture of 3-bromo-5-phenoxypyridine (1.80 g, 7.23 mmol), palladium(II) acetate (15 mg, 0.067 mmol), tri-o-tolylphosphine (80.9 mg, 0.266 mmol), 3-buten-1-ol (494 mg, 6.85 mmol), triethylamine (2.5 mL), and acetonitrile (5 mL) was stirred and heated under reflux for 22 h. The reaction was monitored by thin layer chromatography on silica gel eluting with chloroform-methanol (98:2, v/v). Additional palladium(II) acetate (7.5 mg) and tri-o-tolylphosphine (44 mg) were added to the reaction mixture, which was stirred and heated under reflux for an additional 2 h. After cooling to ambient temperature, the mixture was diluted with water (20 mL) and extracted with dichloromethane (3×25 mL). The combined organic layers were washed with water (25 mL), dried (NaSO$_4$), filtered, and concentrated to yield a dark-yellow oil (1.85 g). The product was purified by column chromatography on silica gel, eluting with chloroform-methanol (94:6, v/v). Selected fractions were combined and concentrated. Purification by vacuum distillation gave 0.468 g of (E)-4-[3-(5-phenoxypyridin)yl]-3-buten-1-ol as a viscous, yellow oil, bp 155°–175° C. at 0.15 mm Hg. Further distillation produced an additional 1.270 g of product as a viscous, yellow oil, bp 165°–175° C. at 0.15 mm Hg, for a total yield of 1.738 g (100%).

$^1$H NMR (CD$_2$Cl$_2$, 300 MHz): δ 8.31 (1H, d, J=1.5 Hz), 8.20 (1H, d, J=2.4 Hz), 7.41–7.34 (2H, m), 7.29 (1H, t, J=2.2 Hz), 7.17 (1H, m), 7.04 (2H, m), 6.45 (1H, d, J=16.0 Hz), 6.27 (1H, dt, J=15.9, 7.0 Hz), 3.72 (2H, t, J=6.3 Hz), 2.46 (2H, m), 1.58 (1H, br s).

(E)-N-Methyl-4-[3-(5-phenoxypyridin)yl]-3-buten-1-amine: Under a nitrogen atmosphere, methanesulfonyl chloride (0.66 g, 5.8 mmol) was added dropwise to a stirring, ice-cold solution of (E)-4-[3-(5-phenoxypyridin)yl]-3-buten-1-ol (1.27 g, 5.3 mmol), triethylamine (1.07 g, 10.5 mmol), and tetrahydrofuran (15 mL). The mixture was stirred for 48 h at ambient temperature. The dark-brown mixture was diluted with water (50 mL) and extracted with chloroform (3×50 mL). The combined chloroform extracts were dried (Na$_2$SO$_4$), filtered, and concentrated to a gold oil (0.873 g). Aqueous methylamine (20 mL, 40% solution) was added to the oil, and the mixture was allowed to stir at ambient temperature for 18 h. The solution was basified with 30% NaOH solution to pH 11–12 and extracted with diethyl ether (4×25 mL). The combined ether extracts were dried (Na$_2$SO$_4$), filtered, and concentrated to a yellow syrup. To purify the product, water (50 mL) was added to the residue, and the pH was adjusted to ~8.0 with 30% HCl solution. The resulting solution was extracted with dichloromethane (50 mL). The aqueous layer was separated, the pH was adjusted to 12.5 using 30% NaOH solution, and this alkaline solution was extracted with tert-butyl methyl ether (3×25 mL). Thin layer chromatography analysis on silica gel, eluting with methanol-ammonium hydroxide (10:1, v/v) indicated that the spent dichloromethane layer contained some product. Therefore, water (25 mL) was added to the dichloromethane extract, and the pH was adjusted to 8.0. The aqueous phase was separated, the pH was adjusted to pH 12.5 using 30% NaOH solution, and this solution was extracted with tert-butyl methyl ether (2×25 mL). All tert-butyl methyl ether layers were combined, dried (NaSO$_4$), filtered, and concentrated to yield 106.5 mg (8.0%) of (E)-N-methyl-4-[3-(5-phenoxypyridin)yl]-3-buten-1-amine as a dark-gold oil.

$^1$H NMR (CD$_2$Cl$_2$, 300 MHz): δ 8.30 (1H, d, J=1.8 Hz), 8.18 (1H, d, J=2.7 Hz), 7.38 (2H, m), 7.28 (1H, t, J=2.2 Hz), 7.16 (1H, m), 7.06–7.02 (2H, m), 6.41 (1H, d, J=16.0 Hz), 6.27 (1H, dt, J=16.0, 6.7 Hz), 2.69 (1H, t, J=6.8 Hz), 2.40 (3H, s), 2.42–2.35 (2H, m), 1.60 (1H, br s).

$^{13}$C NMR (CD$_2$Cl$_2$, 75 MHz): δ 156.96, 154.27, 143.19, 140.14, 134.59, 131.77, 130.39, 127.86, 124.36, 122.09, 119.30, 51.03, 35.85, 33.20.

HRMS: Calcd. for C$_{16}$H$_{18}$N$_2$O (M$^+$): m/z 254.141913. Found: 254.142750.

EXAMPLE 4

Sample No. 4 is (E)-N-Methyl-4-[3-(5-isopropoxypyridin)yl]-3-buten-1-amine, which is prepared according to the following procedure.

3-Bromo-5-isopropoxypyridine: Under a nitrogen atmosphere, 2-propanol (30 mL) was added to potassium (2.4 g, 61.4 mmol) at 0° C., and the mixture was stirred at 0° C. for 30 min. To the resulting solution was added 3,5-dibromopyridine (4.74 g, 20.0 mmol) and copper powder (250 mg, 3.9 mmol). The mixture was heated under reflux under a nitrogen atmosphere for 70 h. Upon cooling to ambient temperature, the mixture was concentrated under high vacuum to a solid, which was diluted with water (200 mL) and extracted with diethyl ether (3×150 mL). The combined ether extracts were dried (Na$_2$SO$_4$), filtered, and concentrated by rotary evaporation to a dark-brown oil (3.71 g). Purification by column chromatography on silica gel, eluting with 10→20% (v/v) diethyl ether in benzene afforded 1.38 g (31.9%) of 3-bromo-5-isopropoxypyridine as a volatile, colorless oil.

$^1$H NMR (CDCl$_3$, 300 MHz): δ 8.23 (1H, s), 8.19 (1H, s), 7.31 (1H, t, J=2.1 Hz), 4.54 (1H, septet, J=6.0 Hz), 1.34 (6H, d, J=6.0 Hz).

(E)-4-[3-(5-Isopropoxypyridin)yl]-3-buten-1-ol: Under a nitrogen atmosphere, a mixture of 3-buten-1-ol (296 mg, 4.1 mmol), 3-bromo-5-isopropoxypyridine (864 mg, 4.0 mmol), palladium(II) acetate (9.0 mg, 0.04 mmol), tri-o-tolylphosphine (50.0 mg, 0.16 mmol), triethylamine (1.0 mL), and acetonitrile (2.0 mL) was stirred and heated under reflux for 27 h. Upon cooling to ambient temperature, the mixture was diluted with water (20 mL) and extracted with dichloromethane (2×20 mL). The combined dichloromethane extracts were dried (Na$_2$SO$_4$), filtered, and concentrated by rotary evaporation to give an orange oil (843 mg). Purification by column chromatography on silica gel, eluting with 0→4% (v/v) methanol in ethyl acetate afforded 498 mg (60.1%) of (E)-4-[3-(5-isopropoxypyridin)yl]-3-buten-1-ol as a thick, light-yellow oil.

$^1$H NMR (CDCl$_3$, 300 MHz): δ 8.13 (1H, d, J=1.4 Hz), 8.10 (1H, d, J=2.6 Hz), 7.14 (1H, t, J=2.3 Hz), 6.43 (1H, d, J=16.0 Hz), 6.26 (1H, dt, J=15.9, 7.0 Hz), 4.57 (1H, septet, J=6.0 Hz), 3.76 (2H, t, J=6.2 Hz), 2.49 (2H, dq, J=6.1, 1.2 Hz), 1.66 (1H, br s), 1.33 (6H, d, J=5.9 Hz).

(E)-N-Methyl-4-[3-(5-isopropoxypyridin)yl]-3-buten-1-amine: Under a nitrogen atmosphere, a cold (0° C.), stirring solution of (E)-4-[3-(5-isopropoxypyridin)yl]-3-buten-1-ol (466 mg, 2.25 mmol), anhydrous dichloromethane (2 mL), and pyridine (2 drops) was treated with p-toluenesulfonyl chloride (540 mg, 2.83 mmol). The mixture was allowed to warm to ambient temperature. After stirring 16 h, the solution was concentrated under a stream of nitrogen, and the residue was further dried under high vacuum. The residue was dissolved in N,N-dimethylformamide (5 mL), and a solution of 2N methylamine in tetrahydrofuran (5 mL) was added. After stirring under a nitrogen atmosphere for 24 h at ambient temperature, the solution was diluted with water (25 mL) and extracted with diethyl ether (2×30 mL). The combined ether extracts were washed with water (10 mL) and saturated NaCl solution (20 mL), dried (Na$_2$SO$_4$), filtered, and concentrated by rotary evaporation to a residue (470 mg). Purification by column chromatography on silica gel, eluting with 2.5% (v/v) triethylamine in absolute ethanol afforded 153 mg (30.9%) of (E)-N-methyl-4-[3-(5-isopropoxypyridin)yl]-3-buten-1-amine as a reddish, amber oil.

$^1$H NMR (CDCl$_3$, 300 MHz): δ 8.13 (1H, d, J=1.7 Hz), 8.10 (1H, d, J=2.7 Hz), 7.13 (1H, t, J=2.1 Hz), 6.40 (1H, d, J=16.0 Hz), 6.23 (1H, dt, J=15.9, 6.9 Hz), 4.57 (1H, septet, J=6.1 Hz), 2.73 (2H, t, J=6.9 Hz), 2.46–2.40 (2H, m), 2.45 (3H, s), 2.19 (1H, br s), 1.33 (6H, d, J=6.0 Hz).

$^{13}$C NMR (CDCl$_3$, 75 MHz): δ 154.09, 140.41, 137.77, 133.67, 130.56, 128.17, 119.05, 70.62, 50.90, 36.06, 33.26, 21.94.

HRMS: Calcd. for C$_{13}$H$_{20}$N$_2$O (M$^+$): m/z 220.157563. Found: 220.157686.

EXAMPLE 5

Sample No. 5 is (E)-N-Methyl-4-[3-(5-methoxymethylpyridin)yl]-3-buten-1-amine, which is prepared according to the following procedure.

3-Bromo-5-methoxymethylpyridine: Under a nitrogen atmosphere, a solution of 5-bromonicotinic acid (5.05 g, 25.0 mmol) and thionyl chloride (10 mL) was stirred and heated. The excess thionyl chloride was removed by distillation, and the residue was dried briefly under high vacuum. To the resulting light-yellow solid in dry tetrahydrofuran (40 mL) was added sodium borohydride (1.90 g, 50.0 mmol) at 0° C. under a nitrogen atmosphere. The mixture was stirred 1 h at 0° C. and allowed to warm to ambient temperature. The mixture was added to a cold, saturated aqueous NH$_4$Cl solution (100 mL) and extracted with diethyl ether (3×50 mL). The combined ether extracts were dried (Na$_2$SO$_4$), filtered, and concentrated by rotary evaporation to a semisolid (2.77 g). Thin layer chromatography analysis on silica gel indicated mostly 5-bromonicotinic acid; therefore the semisolid was partitioned between ether and saturated aqueous NaHCO$_3$ solution. The ether layer was separated and concentrated by rotary evaporation to a residue (0.75 g). Purification by column chromatography on silica gel, eluting with ethyl acetate-hexane (1:1, v/v) afforded 379 mg (8.1%) of 3-bromo-5-hydroxymethylpyridine.

Under a nitrogen atmosphere, a solution of 3-bromo-5-hydroxymethylpyridine (379 mg, 2.0 mmol) in dry tetrahydrofuran (10 mL) was treated at ambient temperature with sodium hydride (160 mg, 4.0 mmol, 60% dispersion in mineral oil). After stirring 5 min at ambient temperature, the opaque, yellow mixture was treated with methyl iodide (342 mg, 2.4 mmol). After stirring 2 h at ambient temperature, the mixture was added to cold water (30 mL) and extracted with diethyl ether (3×20 mL). The combined ether extracts were dried (Na$_2$SO$_4$), filtered, and concentrated by rotary evaporation to an orange oil (429 mg). Purification by column chromatography on silica gel, eluting with 15% (v/v) ethyl acetate in hexane afforded 266 mg (65.3%) of 3-bromo-5-methoxymethylpyridine as a colorless oil.

$^1$H NMR (CDCl$_3$, 300 MHz): δ 8.59 (1H, d, J=2.0 Hz), 8.45 (1H, s), 7.83 (1H, m), 4.43 (2H, s), 3.40 (3H, s).

(E)-4-[3-(5-Methoxymethylpyridin)yl]-3-buten-1-ol: Under a nitrogen atmosphere, a mixture of 3-buten-1-ol (108 mg, 1.5 mmol), 3-bromo-5-methoxymethylpyridine (240 mg, 1.2 mmol), palladium(II) acetate (5.0 mg, 0.02 mmol), tri-o-tolylphosphine (25.0 mg, 0.08 mmol), triethylamine (0.5 mL), and acetonitrile (1.0 mL) was stirred and heated under reflux for 21 h. Upon cooling to ambient temperature, the mixture was diluted with water (10 mL) and extracted with dichloromethane (2×10 mL). The combined dichloromethane extracts were dried (Na$_2$SO$_4$), filtered, and concentrated by rotary evaporation to an oil (240 mg). Purification by column chromatography on silica gel, eluting with 0→4% (v/v) methanol in ethyl acetate afforded 148 mg (64.5%) of (E)-4-[3-(5-methoxymethylpyridin)yl]-3-buten-1-ol as an oil.

$^1$H NMR (CDCl$_3$, 300 MHz): δ 8.47 (1H, d, J=1.8 Hz), 8.37 (1H, d, J=1.6 Hz), 7.66 (1H, t, J=2.1 Hz), 6.47 (1H, d, J=16.0 Hz), 6.32 (1H, dt, J=16.0, 6.9 Hz), 4.44 (2H, s), 3.77 (2H, t, J=6.2 Hz), 3.39 (3H, s), 2.50 (2H, dq, J=6.3, 1.2 Hz), 1.66 (1H, br s).

(E)-N-Methyl-4-[3-(5-methoxymethylpyridin)yl]-3-buten-1-amine: Under a nitrogen atmosphere, a cold (0° C.), stirring solution of (E)-4-[3-(5-methoxymethylpyridin)yl]-3-buten-1-ol (140 mg, 0.72 mmol), anhydrous dichloromethane (1 mL), and pyridine (1 drop) was treated with p-toluenesulfonyl chloride (172 mg, 0.90 mmol). The mixture was allowed to warm to ambient temperature. After stirring 12 h, the solution was concentrated under a stream of nitrogen, and the residue was further dried under high vacuum. The residue was dissolved in N,N-dimethylformamide (2 mL) and treated with 40% aqueous methylamine solution (1 mL) at 0° C. After stirring under a nitrogen atmosphere for 7 h at ambient temperature, the solution was added to 1M NaOH solution (10 mL) and extracted with diethyl ether (2×10 mL). The combined ether extracts were dried (Na$_2$SO$_4$), filtered, and concentrated by rotary evaporation to a residue (99 mg). Purification by column chromatography on silica gel, eluting with 2.5% (v/v) triethylamine in methanol afforded 24 mg (16.1%) of (E)-N-methyl-4-[3-(5-methoxymethylpyridin)yl]-3-buten-1-amine as a light-yellow oil.

$^1$H NMR (CDCl$_3$, 300 MHz): δ 8.47 (1H, d, J=2.1 Hz), 8.37 (1H, d, J=1.9 Hz), 7.65 (1H, t, J=2.0 Hz), 6.43 (1H, d,

J=16.0 Hz), 6.29 (1H, dt, J=16.0, 6.7 Hz), 4.44 (2H, s), 3.39 (3H, s), 2.73 (2H, t, J=6.9 Hz), 2.45 (3H, s), 2.43 (2H, m), 1.56 (1H, br s).

$^{13}$C NMR (CDCl$_3$, 75 MHz): δ 147.54, 147.50, 133.29, 132.88, 131.82, 131.08, 127.88, 72.08, 58.39, 51.14, 36.36, 33.56.

HRMS: Calcd. for C$_{12}$H$_{18}$N$_2$O (M$^+$): m/z 206.141913. Found: 206.142612.

EXAMPLE 6

Sample No. 6 is (E)-4-(3-pyridinyl)-3-buten-1-amine difumarate, which is prepared according to the following techniques.

(E)-4-(3-Pyridinyl)-3-buten-1-amine: This compound was prepared essentially in accordance with the techniques described in W. Frank, et al., *J. Org. Chem.* 43: 2947 (1978).

(E)-4-(3-Pyridinyl)-3-buten-1-amine Difumarate:

(E)-4-(3-pyridinyl)-3-buten-1-amine was converted to its difumarate, mp 164.5°–167° C.

$^1$H NMR (DMSO-d$_6$, 300 MHz): δ 8.70 (1H, d), 8.52 (1H, d), 7.94 (1H, d), 7.45 (1H, dd), 6.65 (4H, s), 6.63 (1H, d), 6.49 (1H, dt), 2.96 (2H, t), 2.52 (2H, m).

$^{13}$C NMR (DMSO-d$_6$, 75 MHz): δ 167.2, 148.3, 147.7, 134.7, 132.6, 132.5, 128.7, 128.4, 123.7, 38.2, 30.5.

EXAMPLE 7

Sample No. 7 is (E)-N-Methyl-4-[3-(5-ethoxypyridin)yl]-3-buten-1-amine Sesquifumarate, which is prepared according to the following procedure.

(E)-N-Methyl-4-[3-(5-ethoxypyridin)yl]-3-buten-1-amine is prepared in accordance with the techniques set forth in U.S. patent application Ser. No. 08/631,762, already incorporated herein by reference in its entirety.

Under a nitrogen atmosphere, fumaric acid (165 mg, 1.18 mmol) was added to a solution of (E)-N-methyl-4-[3-(5-ethoxypyridin)yl]-3-buten-1-amine (244 mg, 1.18 mmol) in 2-propanol (15 mL). After stirring 30 min at ambient temperature, the solution was concentrated by rotary evaporation to a light-brown solid. The solid was dissolved in a mixture of 2-propanol (6 mL) and ethanol (1 mL), assisted by warming. The resulting solution was treated with decolorizing carbon, filtered, and cooled at −20° C. for 5 days. The crystalline solids were filtered, collected, and dissolved in a mixture of ethanol (3 mL) and methanol (1 mL). This solution was filtered through a sintered glass funnel to remove insoluble matter, and the filtrate was diluted with 2-propanol (4 mL) and cooled at −20° C. The crystalline solids were collected and dried under high vacuum to give 102 mg (26.8%) of (E)-N-methyl-4-[3-(5-ethoxypyridin)yl]-3-buten-1-amine sesquifumarate as a light-tan, crystalline powder, mp 126°–127° C.

$^1$H NMR (D$_2$O, 300 MHz): δ 8.33 (1H, br s), 8.26 (1H, d, J=2.4 Hz), 7.97 (1H, t, J=2.1 Hz), 6.68 (1H, d , J=16.1 Hz), 6.62 (2H, s), 6.52 (1H, dt, J=16.1, 7.0 Hz), 4.27 (2H, q, J 6.9 Hz), 3.24 (2H, t, J=7.0 Hz), 2.74 (3H, s), 2.70 (2H, m), 1.44 (3H, t, J=7.0 Hz).

$^{13}$C NMR (D$_2$O, 75 MHz): δ 175.36, 159.89, 139.88, 137.87, 136.28, 134.56, 132.20, 130.30, 129.07, 68.96, 50.81, 35.73, 32.17, 16.58.

Anal. Calcd for C$_{12}$H$_{18}$N$_2$O•1.5 C$_4$H$_4$O$_4$: C, 56.83; H, 6.36; N, 7.37. Found: C, 56.88; H, 6.43; N, 7.34.

EXAMPLE 8

Sample No. 8 is (E)-N-Methyl-4-[3-(5-phenylpyridin)yl]-3-buten-1-amine, which is prepared according to the following procedure.

3-Bromo-5-phenylpyridine: A mixture of 3,5-dibromopyridine (15.00 g, 63.3 mmol), phenylboronic acid (8.11 g, 66.5 mmol), sodium carbonate (14.09 g, 133.0 mmol), water (100 mL), toluene (400 mL), absolute ethanol (100 mL), and tetrakis(triphenylphosphine)palladium(0) (3.66 g, 3.17 mmol) was stirred and heated under reflux at 92° C. (oil bath temperature) for 19 h. The mixture was cooled to ambient temperature and extracted with dichloromethane (400 mL). The dichloromethane layer was washed with saturated, aqueous NaHCO$_3$ solution, dried (Na$_2$SO$_4$), filtered, and concentrated to a residue. Vacuum distillation using a short-path apparatus produced 10.58 g of a white solid, bp 70°–110° C. at 0.05 mm Hg (lit. bp 100°–101° C. at ~0.1 mm Hg, see Guthikonda, R. N.; DiNinno, F. P. 2-(3-Pyridyl)carbapenam Antibacterial Agents. U.S. Pat. No. 5,409,920 (Merck and Co., Inc.), 950425). Further purification by column chromatography on silica gel, eluting with hexane-ethyl acetate (5:1, v/v) afforded 8.23 g (55.5%) of 3-bromo-5-phenylpyridine as a white solid, mp 45°–46° C., R$_f$ 0.50 (hexane-ethyl acetate (5:1, v/v)).

$^1$H NMR (CDCl$_3$, 300 MHz): δ 8.74 (1H, d, J 1.7 Hz), 8.64 (1H, d, J=1.9 Hz), 8.01 (1H, t, J=2.0 Hz), 7.56–7.38 (5H, m). $^{13}$C NMR (CDCl$_3$, 75 MHz): δ 149.35, 146.38, 138.27, 136.86, 136.31, 129.20, 128.69, 127.18, 120.91. HRMS: Calcd. for C$_{11}$H$_8$BrN (M$^+$): m/z 232.984010. Found: 232.984177.

(E)-4-[3-(5-Phenylpyridin)yl]-3-buten-1-ol: Under a nitrogen atmosphere, a mixture of 3-buten-1-ol (476 mg, 6.6 mmol), 3-bromo-5-phenylpyridine (1.50 g, 6.4 mmol), palladium(II) acetate (14.4 mg, 0.064 mmol), tri-o-tolylphosphine (78.0 mg, 0.256 mmol), triethylamine (2.5 mL), and acetonitrile (5.0 mL) was stirred and heated under reflux at 90° C. (oil bath temperature) for 18 h. Upon cooling to ambient temperature, the mixture was diluted with water (25 mL) and extracted with dichloromethane (4×25 mL). The combined dichloromethane extracts were washed with water (25 mL), dried (NaSO$_4$), filtered, and concentrated by rotary evaporation to give a dark-green oil (1.69 g). Vacuum distillation using a test-tube apparatus gave 873 mg of a yellow oil, bp 60°–80° C. at 0.05 mm Hg. Further purification by column chromatography on silica gel (60 g), eluting in succession with hexane-ethyl acetate (5:1, v/v), hexane-ethyl acetate (1:1, v/v), and ethyl acetate afforded 604 mg (41.8%) of (E)-4-[3-(5-phenylpyridin)yl]-3-buten-1-ol as a yellow oil, R$_f$ 0.27 (ethyl acetate).

$^1$H NMR (CDCl$_3$, 300 MHz): δ 8.66 (1H, d, J=2.0 Hz), 8.54 (1H, d, J=1.9 Hz), 7.83 (1H, t, J=2.1 Hz), 7.58–7.54 (2H, m), 7.49–7.36 (3H, m), 6.54 (1H, d, J=15.9 Hz), 6.38 (1H, dt, J=15.9, 6.9 Hz), 3.80 (2H, t, J=6.3 Hz), 2.53 (2H, dq, J=6.3, 1.2 Hz), 1.78 (1H, br s).

(E)-N-Methyl-4-[3-(5-phenylpyridin)yl]-3-buten-1-amine: Under a nitrogen atmosphere, a cold (0° C.), stirring solution of (E)-4-[3-(5-phenylpyridin)yl]-3-buten-1-ol (577 mg, 2.56 mmol), anhydrous dichloromethane (4 mL), and pyridine (1 drop) was treated with p-toluenesulfonyl chloride (537 mg, 2.82 mmol). The mixture was allowed to warm to ambient temperature. After stirring 17 h, the solution was concentrated by rotary evaporation, and the residue was further dried under high vacuum. The resulting brown gum was dissolved in tetrahydrofuran (5 mL) and 40% aqueous methylamine (5 mL) was added. The solution was stirred 6 h at ambient temperature and was then concentrated by rotary evaporation to a brown gum. The residue was partitioned between 1M NaOH solution (10 mL) and chloroform (10 mL). The aqueous phase was separated and extracted with chloroform (2×10 mL). The combined chloroform extracts were washed with water (10 mL), dried (Na$_2$SO$_4$), filtered, and concentrated by rotary evaporation to give a dark-brown residue. To purify the product, water (25 mL) was added to the residue, and the pH was adjusted to 8.2 with 30% HCl solution. The resulting solution was extracted with dichloromethane (2×10 mL); the dichloromethane extracts were subsequently discarded following thin layer chromatography analysis on silica gel. The pH of the aqueous phase was raised to 12.5 using 30% NaOH solution; the product was extracted with tert-butyl methyl ether (3×10 mL). The combined tert-butyl methyl ether extracts were washed with water (10 mL), dried (Na$_2$SO$_4$), filtered, and concentrated by rotary evaporation to give 589 mg of a dark-brown oil. Purification by column chromatography on silica gel, eluting with ethyl acetate produced 95.1 mg of (E)-4-[3-(5-phenylpyridin)yl]-3-buten-1-ol. Subsequent elution with methanol-ammonium hydroxide (9:1, v/v) afforded 82.3 mg (13.5%) of (E)-N-methyl-4-[3-(5-phenylpyridin)yl]-3-buten-1-amine as a dark-brown oil.

$^1$H NMR (CD$_3$OD, 300 MHz): δ 8.63 (1H, br s), 8.52 (1H, br s), 8.11 (1H, t, J=1.9 Hz), 7.69–7.65 (2H, m), 7.53–7.40 (3H, m), 6.65 (1H, d, J=16.0 Hz), 6.52 (1H, dt, J=15.9, 6.7 Hz), 2.89 (2H, t, J=6.7 Hz), 2.59–2.49 (2H, m), 2.52 (3H, s). MS (ESI): m/z 239 (M+H)$^+$. HRMS: Calcd. for C$_{16}$H18N$_2$ (M$^+$): m/z 238.146999. Found: 238.146600.

EXAMPLE 9

Sample No. 9 is (E)-N-methyl-4-[3-(5-aminopyridin)yl]-3-buten-1-amine, which was prepared according to the techniques described in U.S. Pat. No. 5,597,919 to Dull et al., the subject matter of which is incorporated herein by reference in its entirety.

COMPARISON EXAMPLE

For comparison purposes, Sample No. C-1 is provided. This sample is (S)-(−)-nicotine, which has been reported to have demonstrated a positive effect towards the treatment of various CNS disorders.

EXAMPLE 10

Determination of Log P Values

Log P values (log octanol/water partition coefficient), which have been used to assess the relative abilities of compounds to pass across the blood-brain barrier (Hansch, et al., *J. Med. Chem.* ii: 1 (1968)), were calculated according to methods described in Hopfinger, *Conformational Properties of Macromolecules,* Academic Press (1973) using Cerius$^2$ software package by Molecular Simulations, Inc.

EXAMPLE 11

Determination of Binding to Relevant Receptor Sites

Binding of the compounds to relevant receptor sites was determined in accordance with the techniques described in U.S. Pat. No. 5,597,919 to Dull et al., the subject matter of which is already incorporated herein by reference in its entirety. Inhibition constants (Ki values), reported in nM, were calculated from the IC$_{50}$ values using the method of Cheng et al., *Biochem, Pharmacol.* 22: 3099 (1973). Data are presented in Table I.

EXAMPLE 12

Determination of Dopamine Release

Dopamine release was measured using the techniques described in U.S. Pat. No. 5,597,919 to Dull et al., the subject matter of which is already incorporated herein by reference in its entirety. Release is expressed as a percentage of release obtained with a concentration of (S)-(−)-nicotine resulting in maximal effects. Reported EC$_{50}$ is expressed in nM and E$_{max}$ represent the amount released relative to nicotine. Data are presented in Table I.

EXAMPLE 13

Determination of Interaction with Muscle

The determination of the interaction of the compounds with muscle receptors was carried out in accordance with the techniques described in U.S. Pat. No. 5,597,919 to Dull et al., the subject matter of which is already incorporated herein by reference in its entirety. The muscle tissues employed are representative of cells which do not contain β2 receptors. The maximal activation for individual compounds (E$_{max}$) was determined as a percentage of the maximal activation induced by (S)-(−)-nicotine. Data are presented in Table I.

EXAMPLE 14

Determination of Interaction with Ganglia

The determination of the interaction of the compounds with ganglionic receptors was carried out in accordance with the techniques described in U.S. Pat. No. 5,597,919 to Dull et al., the subject matter of which is already incorporated herein by reference in its entirety. The ganglionic tissues employed are representative of cells which do not contain β2 receptors. The maximal activation for individual compounds (E$_{max}$) was determined as a percentage of the maximal activation induced by (S)-(−)-nicotine. Data are presented in Table I.

TABLE I

| Sample No. | Log P | Ki (nM) | E$_{max}$ | EC$_{50}$ (nM) | Muscle Effect (% nicotine) | Ganglion Effect (% nicotine) |
|---|---|---|---|---|---|---|
| C-1* | 0.71 | 2 | 100 | 115 | 100 | 100 |
| 1 | 3.22 | 5 | 33 | 4000 | 12 | 0 |
| 2 | 1.14 | 79 | 107 | 2400 | 8 | 11 |
| 3 | 2.69 | 21 | 14 | 114 | 5 | <15 |
| 4 | 2.43 | 6 | 57 | 51 | 8 | <15 |
| 5 | 1.22 | 130 | 46 | 16,000 | 13 | 0 |
| 6 | 1.38 | 119 | 81 | 5020 | 15 | 23 |
| 7 | 2.37 | 5 | 70 | 276 | 3 | <15 |
| 8 | 3.10 | 184 | >160 | >100,000 | 8 | 0 |
| 9 | 0.32 | 658 | 85 | 2000 | 4 | 4 |

*Sample C-1 is a control and is not an example of the invention

The data in Table I indicate that the compounds have the capability of passing the blood-brain barrier by virtue of their favorable log P values, binding to high affinity CNS nicotinic receptors as indicated by their low binding constants, and activating CNS nicotinic receptors of a subject and causing neurotransmitter release, thereby demonstrating known nicotinic pharmacology. Thus, the data indicate that such compounds have the capability of being useful in treating CNS disorders involving nicotinic cholinergic systems. Furthermore, the data indicate that the compounds do not cause any appreciable effects at muscle sites and ganglionic sites, thus indicating a lack of undesirable side effects in subjects receiving administration of those compounds.

The foregoing is illustrative of the present invention and is not to be construed as limiting thereof. The invention is defined by the following claims, with equivalents of the claims to be included therein.

That which is claimed is:

1. A method for providing prevention or treatment of a central nervous system disorder comprising administering to a subject in need thereof, an effective amount of a compound of the formula:

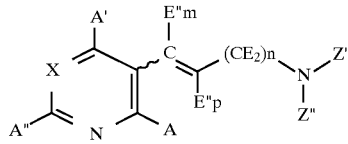

wherein

X is C—R', C—OR', C—CH$_2$—OR' wherein R' is selected from the group consisting of an aromatic group containing species and alkyl-, halo-, or amino-substituted aromatic group containing species;

E' is hydrogen or C$_1$–C$_5$ alkyl or halo substituted C$_1$–C$_5$ alkyl;

E" is C$_1$–C$_5$ alkyl or halo substituted C$_1$–C$_5$ alkyl;

Z' and Z" are each individually selected form the group consisting of hydrogen, C$_1$–C$_5$ alkyl, aryl rings, and can form a ring structure,

A, A' and A" are each individually selected from the group consisting of hydrogen, C$_1$–C$_7$ alkyl, and halo;

m is 0 or 1;

p is 0 or 1 with the proviso that when m or p or both are 0 then E" is hydrogen; and the wavy line in the structure represents a cis (Z) or trans (E) form of the compound.

2. The method according to claim 1, wherein said CNS disorder is a neurodegenerative disease.

3. The method according to claim 1, wherein the central nervous system disorder is selected from the group consisting of Parkinsonism, Parkinson's Disease, Tourette's Syndrome, attention deficit disorder, schizophrenia, and senile dementia of the Alzheimers type.

4. The method according to claim 1, wherein the compound is (E)-N-methyl-4-[3-(5-benzyloxypyridin)yl]-3-buten-1-amine.

5. The method according to claim 1, wherein the compound is (E)-N-methyl-4-[3-(5-phenoxypyridin)yl]-3-buten-1-amine.

6. The method according to claim 1, wherein the compound is (E)-N-methyl-4-[3-(5-phenylpyridin)yl]-3-buten-1-amine.

7. The method according to claim 1, wherein the amount effective to prevent or treat a central nervous system disorder is at least about 25 mg/patient/24 hours and does not exceed about 500 mg/patient/24 hours.

8. The method according to claim 1, wherein the amount effective to prevent or treat said a central nervous system disorder is at least 10 g/patient/24 hours and does not exceed about 400 g/patient/24 hours.

9. The method according to claim 1, wherein the amount of the compound of formula I administered is such that the subject does not experience a concentration of compound in plasma which exceeds 500 ng/ml.

10. The method according to claim 1, wherein X is C—R'; R' is selected from the group consisting of an aromatic group containing species and alkyl-, halo-, or amino-substituted aromatic group containing species; n is an integer which ranges from 1 to 3; Z' and Z" individually represent hydrogen, methyl or isopropyl; A and A' represent hydrogen; A" represents hydrogen, methyl or ethyl; m is 0 and p is 0.

11. The method according to claim 1, wherein X is C—OR'; R' is selected from the group consisting of an aromatic group containing species and alkyl-, halo-, or amino-substituted aromatic group containing species; n is an integer which ranges from 1 to 3; Z' and Z" individually represent hydrogen, methyl or isopropyl; A and A' represent hydrogen; A" represents hydrogen, methyl or ethyl, m is 0 and p is 0.

12. The method according to claim 1, wherein X is C—CH$_2$—OR', R' is selected from the group consisting of an aromatic group containing species and alkyl-, halo-, or amino-substituted aromatic group containing species; n is an integer which ranges from 1 to 3; Z' and Z" individually represent hydrogen, methyl or isopropyl; A and A' represent hydrogen; A" represents hydrogen, methyl or ethyl, m is 0 and p is 0.

* * * * *